(12) United States Patent
Rusin et al.

(10) Patent No.: US 9,830,801 B2
(45) Date of Patent: Nov. 28, 2017

(54) ALARM MANAGEMENT SYSTEM

(71) Applicant: Medical Informatics Corp., Houston, TX (US)

(72) Inventors: Craig Rusin, Houston, TX (US); Emma Fauss, Houston, TX (US)

(73) Assignee: Medical Informatics Corp., Houston, TX (US)

( * ) Notice: Subject to any disclaimer, the term of this patent is extended or adjusted under 35 U.S.C. 154(b) by 0 days.

(21) Appl. No.: 14/548,376

(22) Filed: Nov. 20, 2014

(65) Prior Publication Data

US 2015/0137968 A1 May 21, 2015

Related U.S. Application Data

(60) Provisional application No. 61/906,714, filed on Nov. 20, 2013.

(51) Int. Cl.
G08B 25/00 (2006.01)
G06F 19/00 (2011.01)

(52) U.S. Cl.
CPC ............ G08B 25/001 (2013.01); *G06F 19/30* (2013.01); *G06F 19/34* (2013.01)

(58) Field of Classification Search
CPC ... G08B 25/001; G06F 19/34; G06F 19/3418; G06F 19/3431; G06F 19/30; G06F 19/32; G06F 19/327
See application file for complete search history.

(56) References Cited

U.S. PATENT DOCUMENTS

| | | | | |
|---|---|---|---|---|
| 2007/0198295 | A1* | 8/2007 | Duckert | G06F 19/327 705/2 |
| 2007/0253021 | A1* | 11/2007 | Mehta | A61B 5/0002 358/1.15 |
| 2013/0045685 | A1* | 2/2013 | Kiani | G06F 19/3406 455/41.2 |
| 2013/0162424 | A1* | 6/2013 | Treacy | G06F 19/327 340/502 |
| 2014/0031643 | A1* | 1/2014 | An | A61B 5/0205 600/309 |
| 2014/0132413 | A1* | 5/2014 | Fox | A61B 5/0022 340/573.1 |
| 2015/0221194 | A1* | 8/2015 | Sarkar | G08B 13/2465 340/870.16 |

* cited by examiner

Primary Examiner — Hongmin Fan
(74) Attorney, Agent, or Firm — Blank Rome LLP

(57) ABSTRACT

The Alarm Management System allows hospitals and critical care units to manage alarms generated by patient monitors and includes the following components: The Alarm Dashboard provides a display of alarm history and trends categorized as desired by hospital administrators. The Alarm Criticality Discernment Tool assists in distinguishing between critical and non-critical alarms. This Tool can allow a clinician to accommodate patient-specific or doctor-specific rules, alarm thresholds, or exceptions. The Alarm Renderer Tool provides physiological data for a predetermined period before the alarm and upon receiving a patient alarm, allows the alarm and the physiological data displayed visually to be forwarded to a care provider to assist in the determination of the criticality of the alarm. The Alarm Router Tool is a set of rules and editor for routing and escalating unacknowledged alarms to other care providers and recording these events.

17 Claims, 14 Drawing Sheets

ALARM MANAGEMENT SYSTEM

TECHNICAL FIELD

The present invention relates to the field of managing alarms in a hospital setting and, in particular, to techniques for understanding the alarm generation environment in this setting, distinguishing critical from non-critical alarms and managing routing of alarms.

BACKGROUND ART

Hospital Intensive Care Unit (ICU) workers are overwhelmed by alarms. Chemical and power industry standards for alarms provide that that one worker should be asked to respond to no more than 100-300 alarms per 12 hour shift. ICU nurses are routinely asked to respond to greater than 300 alarms in a shift (in some instances, greater than 1000), the vast majority (95%) of which are false or non-critical. The Joint Commission which accredits and certifies more than 20,000 health care organizations and programs in the United States, in 2013 issued a white paper outlining the problems of alarm fatigue, declaring it a frequent and persistent problem, and outlining proposals for alarm management.

In order to evaluate any change in alarm management, it is important to be able to initially quantify and monitor the alarm problem. By gathering relevant data at inception, any change, whether operational or due to an adjustment in alarm configuration and settings, can be measured. Currently there is no commercial solution to both continuously monitor the alarm environment, apply layers of intelligence to an alarm management solution, and compare the alarms to what is actually happening with the patient.

BRIEF DESCRIPTION OF DRAWINGS

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

Figure 1:
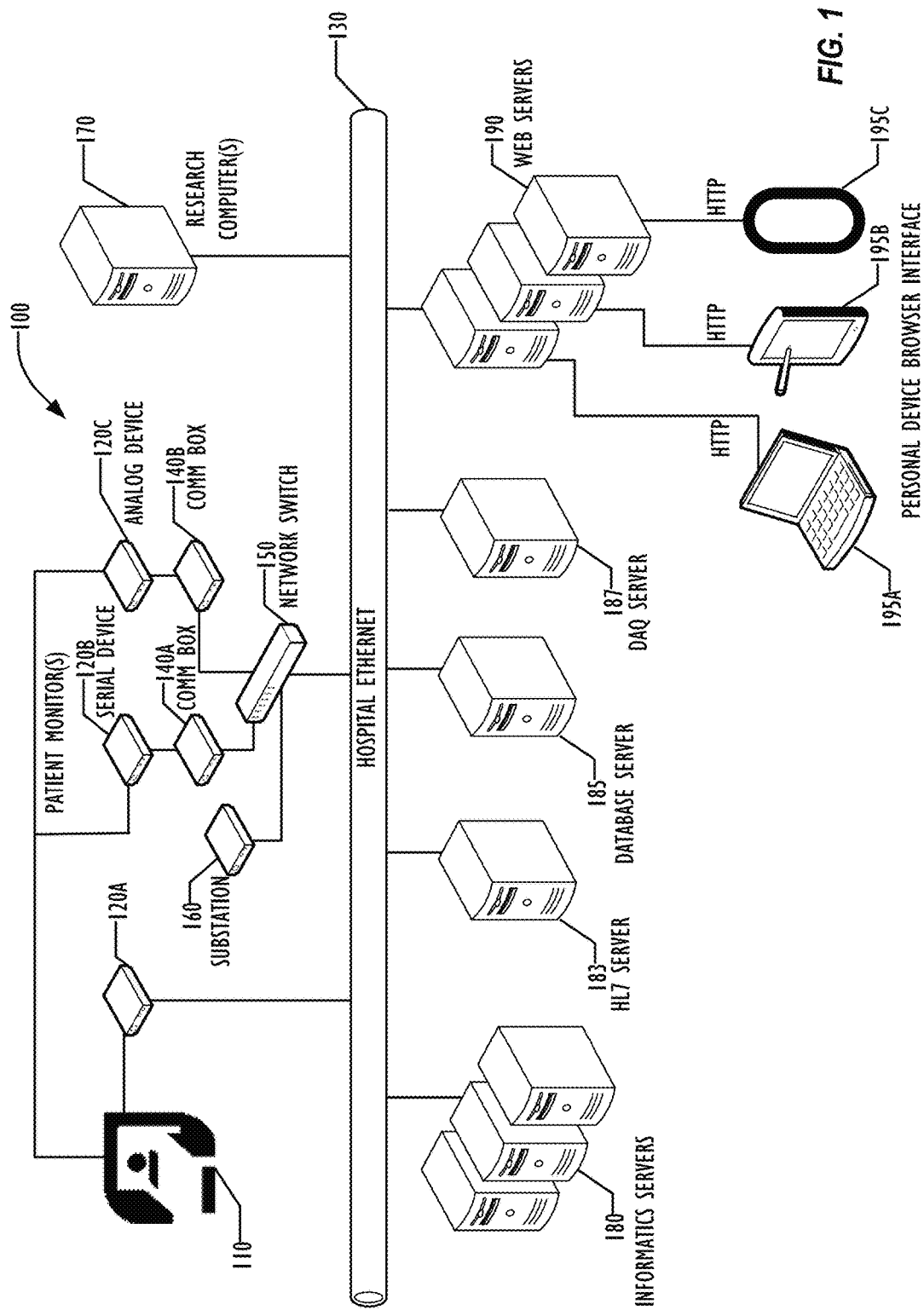
FIG. 1 is a block diagram illustrating a network of devices employed by a hospital system according to one embodiment.

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts are understood to reference all instance of subscripts corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Although some of the following description is written in terms that relate to software or firmware, embodiments can implement the features and functionality described herein in software, firmware, or hardware as desired, including any combination of software, firmware, and hardware. References to daemons, drivers, engines, modules, or routines should not be considered as suggesting a limitation of the embodiment to any type of implementation.

Although the following description is written in terms of an implementation in an Intensive Care Unit (ICU) and ICU alarms, the invention is not so limited. Embodiments may be implemented in a variety of settings, including without limitation, acute care units and monitoring of any type of health sensors, including home and consumer mobile monitoring devices.

Some current middleware vendors have limited access to device data and often downsample the data to such an extent that it makes meaningful analytics impossible. An example of the data they help capture is patient vital signs (e.g. heart rate, respiratory rate) taken every minute and then pushed to the hospital's electronic medical records (EMR) for storage. EMR storage of patient-specific historical data is very limited in terms of the data that is collected (low resolution, downsampled data from only supported networked devices) as well as its inability to conduct data analysis either retrospectively or in teal-time.

When one product captures and stores patient bedside monitoring data, its data format is proprietary and closed. It provides a single tool which converts the data files into enormous XML files, which the end-user must parse to retrieve specific information. This task is unmanageable for research. Additionally other products may export to Health Level 7 (HL7), a text based format which is equally unsuitable for research. (HL7 refers to a set of international standards for transferring clinical and administrative data between hospital information systems, and are produced by Health Level Seven International, Inc.) There are limitations of such systems: such systems do not have a reliable timestamp and provide data through a spreadsheet with a limited viewing tool rather than through an analysis-friendly tool. Additionally, such systems do not have the ability to capture data from ancillary, non-networked patient monitoring devices.

Another product redisplays bedside monitor data in real-time for clinical use but does not archive the data for research or make it available for analysis. It also does not have the ability to capture data from ancillary, non-networked devices. It also does not have the ability to export this data for subsequent analysis.

The system described herein can capture all the physiological data on the network and on any monitor device with a serial or analog port. The majority of physiological monitoring devices have a serial or analog port. For purposes of this discussion, a serial device is one that provides a serial, non-networked output and an analog device is a non-networked device that provides an analog output signal. Embodiments of the system timestamp the data in its archive to within a predetermined level of accuracy, allowing synchronization of data and analysis of data across the various input sources. The system can perform calculations on the data in real-time.

Embodiments of the system can provide the data to an external numerical computing environment available to researchers for analysis, in addition to providing its own data analysis tools. One such external environment is the MATLAB® environment. (MATLAB is a registered trademark of The Mathworks, Inc.)

The system comprises five types of servers, in addition to various data acquisition devices: data acquisition servers, database servers, informatics servers, and visualization servers. Embodiments may employ one or more of each type of server. In addition, external computers, may connect to the system for research analysis of the collected data.

A structured query language (SQL) database is used to hold the index for data storage location in the file system, rather than the actual data files. A unique technique assures both networked and non-networked devices provide timestamps for data that are accurate and synchronized to within 40 milliseconds, allowing correlating collected data.

In one embodiment, a clinical research format (CRF) data format allows recording of an arbitrary number of signals with an arbitrary frame-rate with an arbitrary sampling rate, where
  1) The number of signals can vary per frame;
  2) The number of samples can vary per signal per frame;
  3) Each signal has a unique identifier; and
  4) Users can create their own set of unique identifiers;

Different frames can have different data types, for example picture, numeric array, eXtended Markup Language (XML), Java Script Object Notation (JSON), text, binary, etc. The data format allows for inclusion of calibration constants.

Embodiments of the system can use distributed processing for real-time physiological data processing, where real-time distributed processing means physiological and associated patient data can be distributed among an arbitrary number of machines for parallel processing and continuous transformation with low latency. For example, a program may be created to process real-time data, which may be designated to run on one of a plurality of informatics servers. The system then executes the program on the designated informatics server. For purposes of this discussion, "real time" is used to mean that "without perceivable delay."

The system can push physiological data to web browsers in real time through a websocket protocol that facilitates real-time 2-way interaction between an informatics server and a web browser. The system converts incoming physiological data streams from various data sources at bedside monitors to the CRF data format. Then the CRF data can be converted to JSON and pushed to a websocket server, which then can use a publish/subscribe model to publish the data to all client browsers in real time. The distribution is push-based, instead of pull-based, allowing distribution to multiple web browsers simultaneously.

The system allows for distributed collection of data from non-networked (serial and analog) devices with buffering. A distributed system allows converting native device data into the CRF format, which is then pushed to a central server for collection and routing. All data collection is synchronized and time stamped. In some embodiments, a medical device sends data to a computer, which sends data to a switch, which sends data to sub-station computer which sends data to data collection server. The substation is used to identify what devices are associated with a particular bed. This bed association allows integrating non-networked data signals with other networked data signals.

The system allows for alarm routing. Alarms are captured by the system, typically as HL7 streams.

Arbitrary calculations may be applied to data streams in the CRF format, transforming the data streams for recognizing false positives and false negatives, as well as for displaying data and new derived metrics. This allows rapid creation of new monitors and monitoring modalities for different users or different diseases. In addition, data fusion of physiological data, labs and medications allows the system to present new alarms and new monitors that may be patient or disease specific, using different pieces of patient data to create new alarms and new monitors. Various embodiments provide the capability of easily combining an arbitrary number of data signals and transforming them into useful information for the user, providing new monitoring modalities.

Data is obtained from various sources, converted to CRF format, and collected in real-time and stored on data servers, allowing data transformation to occur in real-time or on historical data sets.

Various embodiments allow creation of modular monitoring or virtual monitoring, which can be one or more of disease- and patient-specific monitoring, based on the condition of the patient, as defined or decided by a care provider. A doctor can prescribe a type of monitoring on a patient-by-patient basis. Monitor data can be accessed remotely through a website interface.

Data transformations are done on the server; display transformations may be done by a website interface. Multiple transformations can be computed in parallel for a particular patient. Raw data is transcoded into CRF format, routed or distributed to informatics servers, where it can be transformed data using arbitrary transformation. The transformed data can itself be recursively re-routed or distributed, transcoded again, and turned into visualized data.

Distributed clock synchronization is a feature that allows correlating data from a hierarchical network of devices, each with a clock with a certain, possibly different, precision. Because the clocks may drift over time the system uses the Network Time Protocol (NTP) to synchronize data acquisition servers. In one embodiment, the data acquisition servers contacts every substation in every patient room every minute.

In one embodiment, the Data Acquisition (DAQ) server opens a connection to a substation, typically an Internet protocol suite connection, such as a Transmission Control Protocol (TCP) connection. The DAQ server acquires its current time stamp and transfers it to the substation. The substation records its timestamp when the transmission is completed and sends the DAQ server the substation timestamp and the timestamp received from the DAQ server. The DAQ server then calculates the time differential. This procedure is repeated multiple times, and the lowest time differential is sent back to the substation from the DAQ server. The substation uses that differential to reset its internal clock. When the substation received a new time offset, it executes the same procedure to synchronize all of the connected serial or analog devices.

This technique is performed repeatedly. In one embodiment, the technique is replicated every minute, on every substation. The frequency of time synchronization depends on the precision of the internal clocks of the devices in the system, including the substations.

Real-time physiological data can be pushed to any number of clients. A client can subscribe to a data channel as one or both of a data sink and a data source. An arbitrary number of clients can subscribe to a single channel and a single client can subscribe to an arbitrary number of channels. In one embodiment, this is implemented in the informatics server, which provides a multi-threaded distributed system, providing for failover detection and recovery for real-time processing. The informatics system monitors every instantiated process on the informatics server(s) and recognizes when the process abnormally terminates and automatically restarts it.

In one embodiment, the DAQ server polls each archive (informatics) server and requests the amount of free space on each server. Then the DAQ server transfers the file to the informatics server with the most available space. All data acquired for a bed is transferred together to prevent data fragmentation. This helps evenly distribute the data among the existing archive servers.

Websocket server(s) provide a native interface. Data is transcoded from CRF to JSON which is transmitted to the websocket server(s).

Real-time calculations (e.g., new metrics of health) executed on the system can be pushed to HL7 data streams in compliance with international health care informatics standards. Arbitrary calculations may be computed on the informatics servers, the result of which can generate and emit an HL7 message.

The combination of servers allows for modular construction of monitoring from widgets that allow arbitrary display and graphing of data from arbitrary data streams. Modular construction of monitors is provided by using layouts and modular, re-useable widgets for physiological data and other metrics of health, which may or may not be calculated from other physiological data. The professional user, such as a physician, can define their own customized monitor using the modular construction of monitoring. This can be applied on a patient-by-patient basis. Embodiments provide for real-time transcoding of CRF data format to formats such as JSON, HTML, XML, TXT, and HL7 as well as other data formats as desired, and provide the ability to decode and encode the CRF format into various other formats. This allows HL7 integration into an internal data stream. HL7 messages can be decoded into the CRF format and be processed like every other data frame in the system.

Embodiments allow visualization of transformed physiological and patient related data, including both calculated data and measured data. New types of data visualization (e.g., non-standard monitor views) can be generated. The system also provides support for novel metrics of health, such as goal-directed therapies and predictive analytics.

FIG. 1 is a block diagram illustrating a system 100 for collecting, archiving, and processing arbitrary data in a healthcare environment according to one embodiment.

As illustrated, there are five types of servers: the DAQ server 187, the informatics server(s) 180, the database server 185, the HL7 server 183, and the web server(s) 190. Any number of any of the types of servers may be deployed as desired. All of the servers 180-190 connect to each other and the bedside monitors via one or more hospital networks 130. Although illustrated as a single hospital Ethernet network 130, any number of interconnected networks may be used, using any desired networking protocols and techniques.

Also connected to the hospital network 130 are a number of bedside monitors for monitoring physiological data for a patient in bed 110. These bedside monitors may include network connected monitors 120A, which can deliver digital physiological data to the hospital network 130, serial devices 120B, which produce digital data but are not directly connected to a network, and analog devices 120C, which produce analog data and are not directly connected to a network. Communication boxes 140A and 140B allow connecting the serial devices 120B and analog devices 120C, respectively, to the hospital network 130, typically through a network switch 150. In addition, a substation 160 may be also connected to the network 130 via the network switch 150 for performing data manipulation and time synchronization as described below. Any number of bedside monitor devices 120 may be used as determined advisable by physicians and other clinical staff for the patient in bed 110.

Although as illustrated in FIG. 1 the bedside monitors and associated communication devices are connected directly or indirectly to the hospital network 130, remote bedside monitoring devices may be used as part of the system 100, such as home monitoring devices, connected to the hospital network 130 indirectly through the Internet or through other communication techniques.

Additionally, one or more research computers 170 may be connected, directly or indirectly, to the hospital network 130, allowing researchers to access aggregated data collected from bedside monitors 120 for performing analytics and development.

The web servers 190 are configured for communicating with personal devices such as laptop 195A, tablet 195B, or smart phone 195C via a web browser interface using HyperText Transport Protocol (HTTP).

Figure 2:
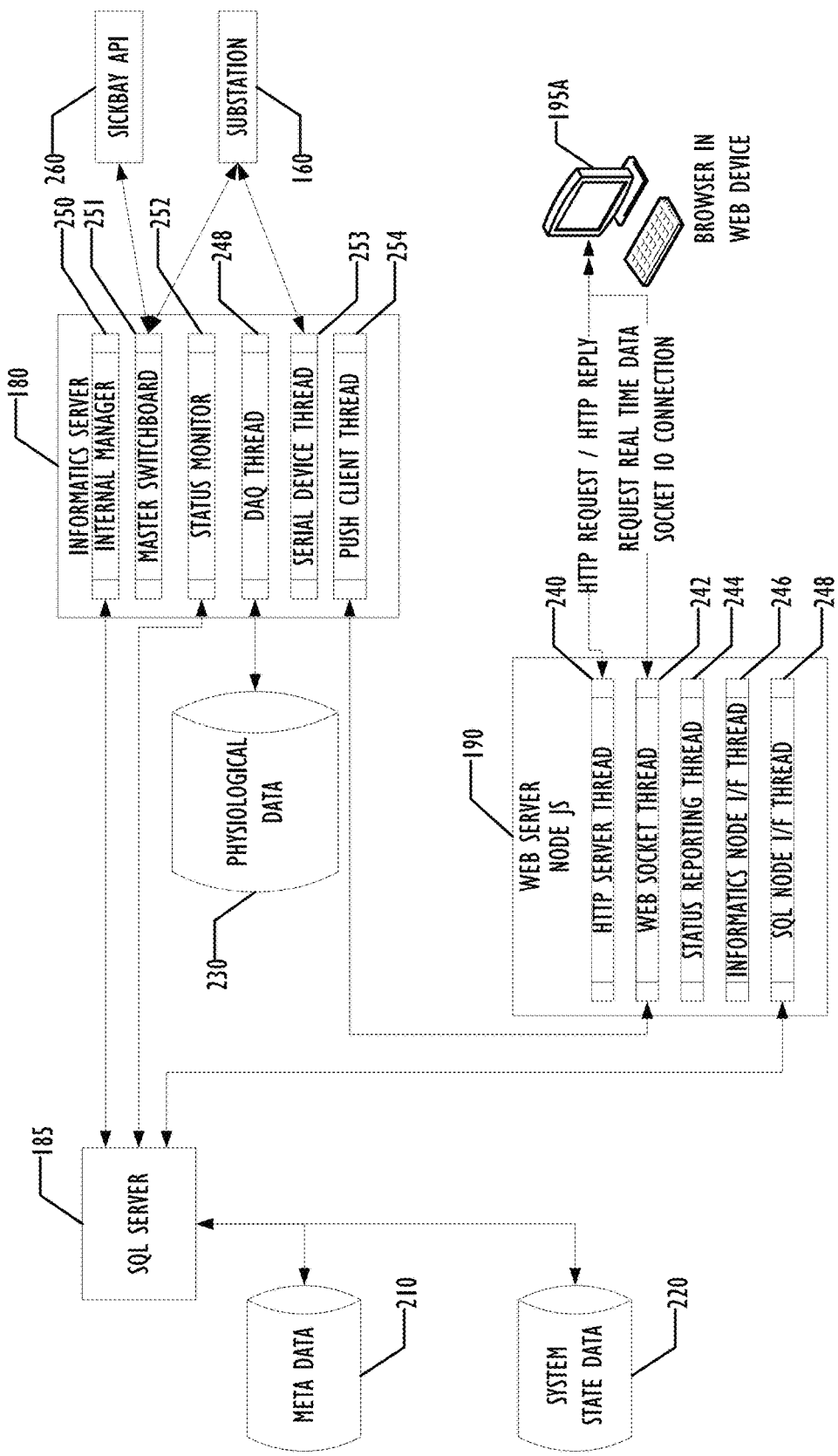
FIG. 2 is a block diagram illustrating communication flows in a hospital system according to one embodiment.

Further details are illustrated in FIG. 2, which is a block diagram illustrating communication flows in the system 100 according to one embodiment. The database server 185 in one embodiment is a Structured Query Language (SQL) server, managing two data collections: metadata 210 and system state data 220. As explained above, rather than keeping the actual patient data in the server 185, the server 185 stores index information pointing to the actual physiological data stored by the informatics server(s) 180. As illustrated in FIG. 2, a storage device is used by the SQL server 185 for storing metadata 210 and a different storage device used for storing system state data 220; however, any number of storage devices may be used, and metadata 210 and system state data 220 may be stored on shared devices as desired and configured for performance purposes. Although illustrated as an SQL server, the database server 185 may use other database technology for storing the metadata 210 and system state data 220 as desired. If an SQL server is used, any type of SQL database system may be used, including PostgreSQL.

Similarly, FIG. 2 illustrates a single storage device 230 for physiological data as binary data, wave forms, etc.; however, any number of storage devices may be used as desired. As described above, multiple informatics servers and multiple storage devices may be used, distributing the data across multiple servers and storage devices as desired for performance reasons.

In one embodiment, the web server 190 may use multiple threads for performing its task of providing an interface to the monitored data. An HTTP server thread 240 may handle HTTP requests and replies for communicating with browsers in user devices 195, such as the laptop 195A illustrated in FIG. 2. Similarly, a websocket thread 242 may be employed for real time data socket I/O connections. Additionally, status reporting thread 244, informatics server node interface thread 246, and database node interface thread 248 may be employed in the web server 190. Similarly, the informatics server 180 may be multi-threaded, with an internal manager thread 250 for communicating with the SQL server 185, a master switchboard thread 251 for communicating with an Application Programming Interface (API) 260 and substations 160, a status monitor thread 252 for monitoring the status of the SQL server 185, a serial device thread 253 for communicating with the substation 160, and a push client thread 254 for communicating with the web socket thread of the web server 190.

Figure 3:
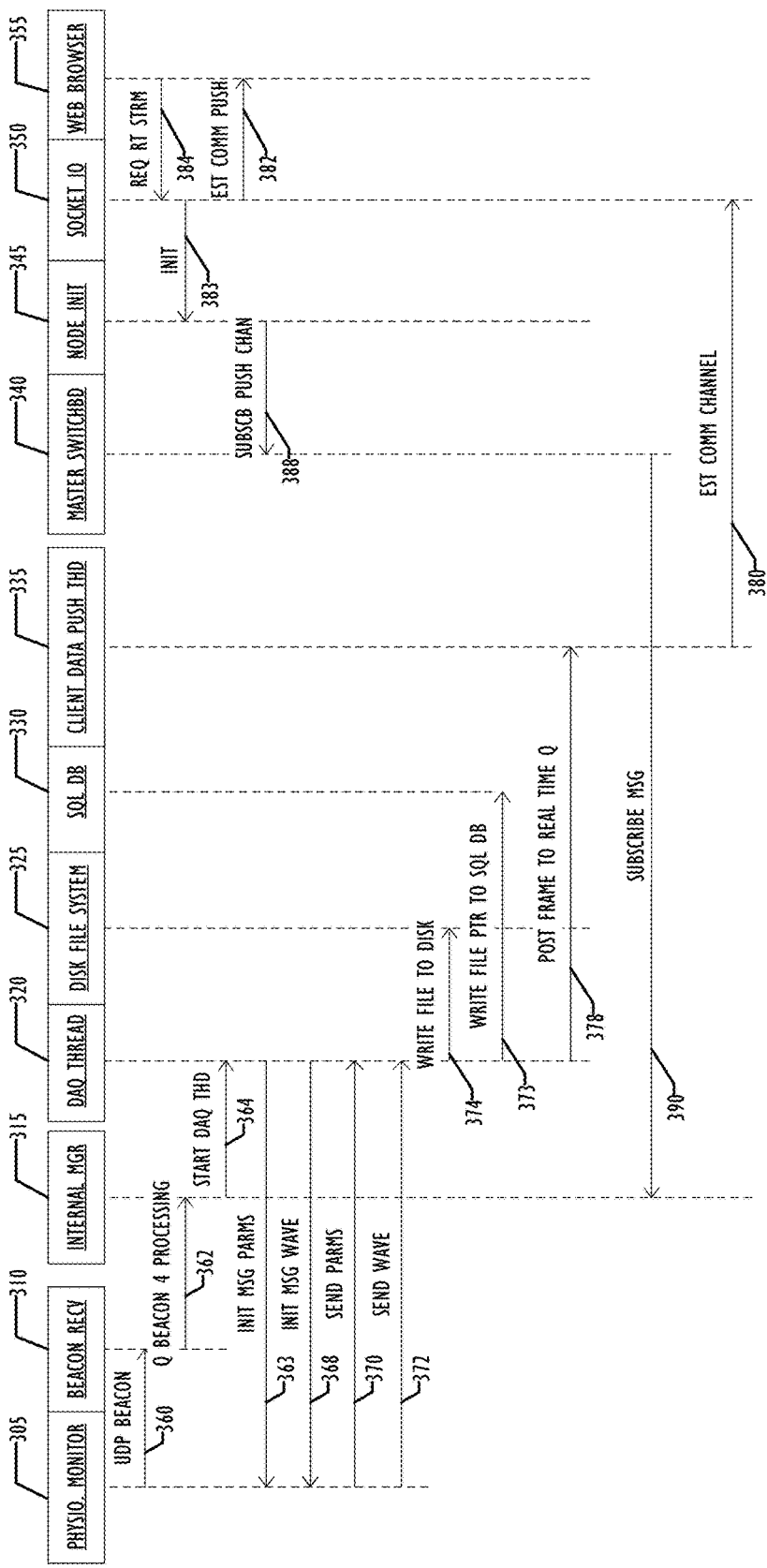
FIG. 3 is a sequence diagram illustrating patient monitor to web browser communication according to one embodiment.

FIG. 3 is a Unified Modeling Language (UML) sequence diagram illustrating bedside monitor to web browser communications in the system 100 according to one embodiment. Physiological monitor 305, which corresponds to one of the bedside monitors 120 of FIG. 1 sends a beacon message 360 to a beacon receiver object 310 in DAQ server 187, which in turn sends a queue beacon for processing message 362 to an internal manager thread 315 of an informatics server 180. The internal manager thread 315 sends a message to a data acquisition thread 320 of the data acquisition server 187 to start acquiring data. The data acquisition thread 320 sends messages 366-372 to the physiological monitor 305, telling the monitor 305 to initialize parameters and waveforms (366, 368), then the monitor 305 sends parameters and waveforms (370, 372) to the data acquisition thread 320. Upon receiving physiological data, the data acquisition thread 320 writes (374) a data file to a disk file system 325 of the informatics server 180 and writes (376) a file pointer to the data file to the SQL database 330 of the database server 185. The data acquisition thread also posts a CRF frame to a real time queue (378) of a client data push thread 335. That thread sends a message (380) to a socket I/O thread 350 of the web server 190 to establish a communication channel. The socket I/O thread 350 sends a establish communications push thread 382 to the web browser 355 of one of the user devices 195, causing it to send a request for a real-time stream (384) back to the socket I/O thread 350.

The socket I/O thread 350 sends an initialization messages 386 to a node initialization object 345, causing it to send a subscribe to push channel messages 388 to master switchboard thread 340. The master switchboard thread 340 then sends a subscribe message 390 to the internal manager thread 315 of the informatics server 180.

Figure 4:
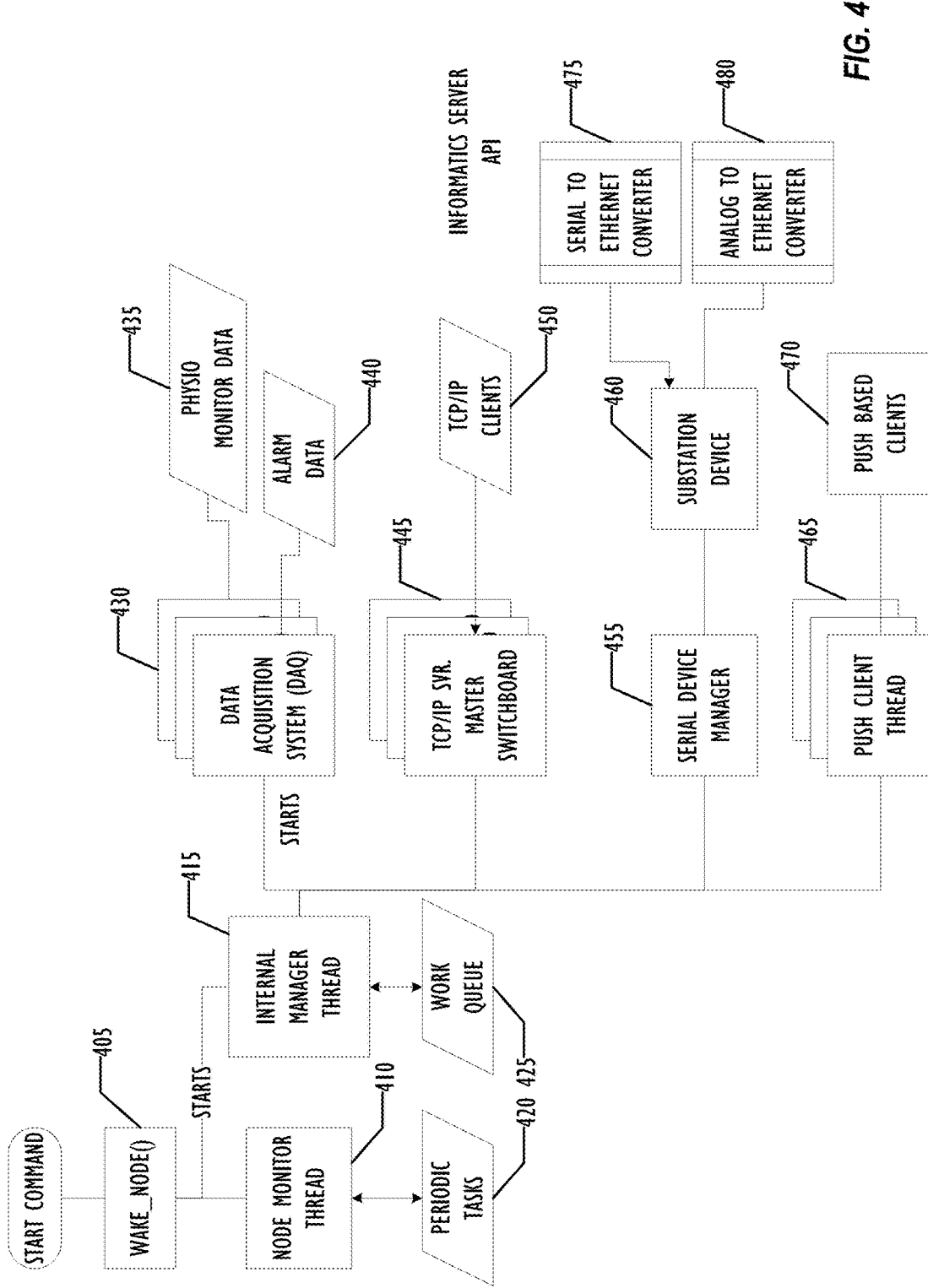
FIG. 4 is a flowchart illustrating a sequence of events occurring during startup of a hospital system according to one embodiment.

FIG. 4 is a flowchart illustrating initialization of the system 100 according to one embodiment. Starting on the informatics server 180, the primary thread of the system 100 is the wake-node thread 405, which is started by a start command. The wake-node thread 405 starts two other threads: the node monitor 410 and the internal manager 415.

The node monitor thread 410 has a list of periodic tasks that the system 100 needs to do, and the node monitor thread 410 places these tasks as commands in an internal manager thread work queue 420. The internal manager thread 415 has a work queue 425 that contains a ranked list of tasks or commands which the internal manager 415 executes by starting new threads.

The internal manager thread 415 starts the following threads:

1) Data Acquisition (DAQ) Subsystem 430, which acquires physiological monitor data 435 and alarm data 440. In one embodiment, the DAQ thread 430 executes on the data acquisition server 187.

2) TCP/IP Server (or Master Switchboard) 445. This thread starts TCP/IP clients 450.

3) Serial Device Manager thread 455. This thread interacts with the substations 460 (corresponding to substations 160 of FIG. 1), which in turn interact with serial to Ethernet converters 475 and analog to Ethernet converters 480, corresponding to the communications boxes 140A, 140B of FIG. 1.

4) Push Client thread 465. This thread interacts with push-based clients 470.

Each of these threads can in parallel read and write to the file system of the informatics server(s) 180 and can in parallel read and write to the SQL database maintained by the database server 185.

The DAQ thread 430 listens on the network for network packets from physiological monitors on the hospital network. Each time a packet is received, its contents are examined to extract the bed identifier, the location on the network, as well as services the device supports. The bed identifier within the packet is compared to the bed filter list maintained by the server informatics server 180. The bed filter list is the list of all bed identifiers for which the server 180 is responsible for recording data. The bed filter list is periodically synchronized with the database table DAQ bed filter. All network packets with bed identifiers which are not on this list will be ignored.

All network packets with bed identifiers within the filter list will be enabled for recording. In one embodiment, when the main data acquisition thread 430 encounters a packet which identifies an active bed which matches the filter criteria and is not currently being recorded, a new DAQ thread 430 is created. In such an embodiment, therefore, the system 100 starts one data collection thread 430 for each bed 110 to be recorded. This new thread 430 will record all of the data being generated from the bed 110.

Network sockets are established for each device for data communication. Multiple vital sign signals can be found in a single packet. Typically multiple signals can be found in each waveform packet. In one embodiment, each signal can be sampled at rates ranging from less than 0.2 Hz to greater than 1 KHz.

The data acquisition system (430) can process packets slightly out of order and overlook lost packets. Each packet has a sequence number associated with it. Additionally, the time between data packets is not necessarily constant. As a result, the data collection system 430 needs to have a way to correct for packet jitter. Since each packet contains data which is evenly sampled, the number of samples can be used as a clock to ensure that the data timestamp is accurate. Drift is expected since the clock on the bedside device 120 is not exactly the same as the server 187's internal clock. Each minute, the offset between the two clocks can be estimated and the clocks re-synced thereby eliminating DAQ clock drift. In addition, where bedside devices, such as serial devices 120B or analog devices 120C do not have clocks, the substation 160 may be used to inject clock data into the packets. Clock drift is similarly handled for packets processed by the substation 160 by synchronizing the clocks periodically.

Time synchronization is done using a distributed hierarchical time synchronization technique. Data acquisition substation devices 160 each have their own master clock and those clocks are synched to a time synchronization server using NTP on a per room basis. Where sensors 120 produce serial or analog data without timestamp data, a converter box (such as communication box 140A/B) is used to add a timestamp. In some embodiments, each hospital room has a data acquisition substation 160 that communicates with the other devices in the room using the network switch 150. The substation's clock may also be synchronized with the data acquisition server 187's clock to avoid time drift, as discussed above.

The DAQ threads 430 also listen for alarms 440 posted on the network and manages the bed list listening for bed assignments and changes in bed assignment.

The Master Switchboard thread 445 uses a high performance architecture for providing asynchronous communication with clients. Clients can include, but are not limited to a MATLAB interface for communicating with the research server 170, and the system web servers 190, and a C Application Programming Interface (API) library which can be integrated into third party programs such as the LABVIEW® software (LABVIEW is a registered trademark of National Instruments Company).

The Serial Device Manager thread 455 manages data from all the serial and analog non-networked devices 120B and 120C that communicate via substations 460. Periodically, this thread will check the status of all of the serial and analog data collection devices on the network. In one embodiment, HTTP retrieval is performed for records as well as web-sockets (signals, labs, meds) using a representational state transfer (REST) interface.

The serial device manager thread 455 also can perform remote firmware upgrades when necessary, and synchronize the clock on the non-networked devices with the local master clock on the server 187, and push out additional configuration settings if necessary.

The Push Client Manager thread 465 manages all of the outgoing push-based data streaming clients. When a new push-based client (e.g., a websocket client) is registered, thread 465 creates an outgoing connection to the specified IP address, using the specified protocol. All data from the specified channel is then automatically pushed to this outgoing client connection whenever new data is available. Data is also automatically transcoded into the desired format. In one embodiment, for websocket-based clients, all data is transcoded into JSON format.

In one embodiment, the system 100 uses an SQL database to hold all of the state full information regarding all system operations. The other servers poll the database for changes in its state.

The system webserver(s) 190 enable standard web browsers to access all the functionality of the system 100. The system webserver 190 in one embodiment is built on top of the Node.JS® platform (NODE.JS is a registered trademark of Joyent, Inc.) and is composed of two components, an HTTP server which serves the web pages associated with the system 100, and the WebSocket server which provides the mechanism for real-time data streaming from the informatics server to the client's browser 195. The real-time data streaming uses a publish-subscribe architecture for disseminating real-time physiological data to web clients.

Figure 5:
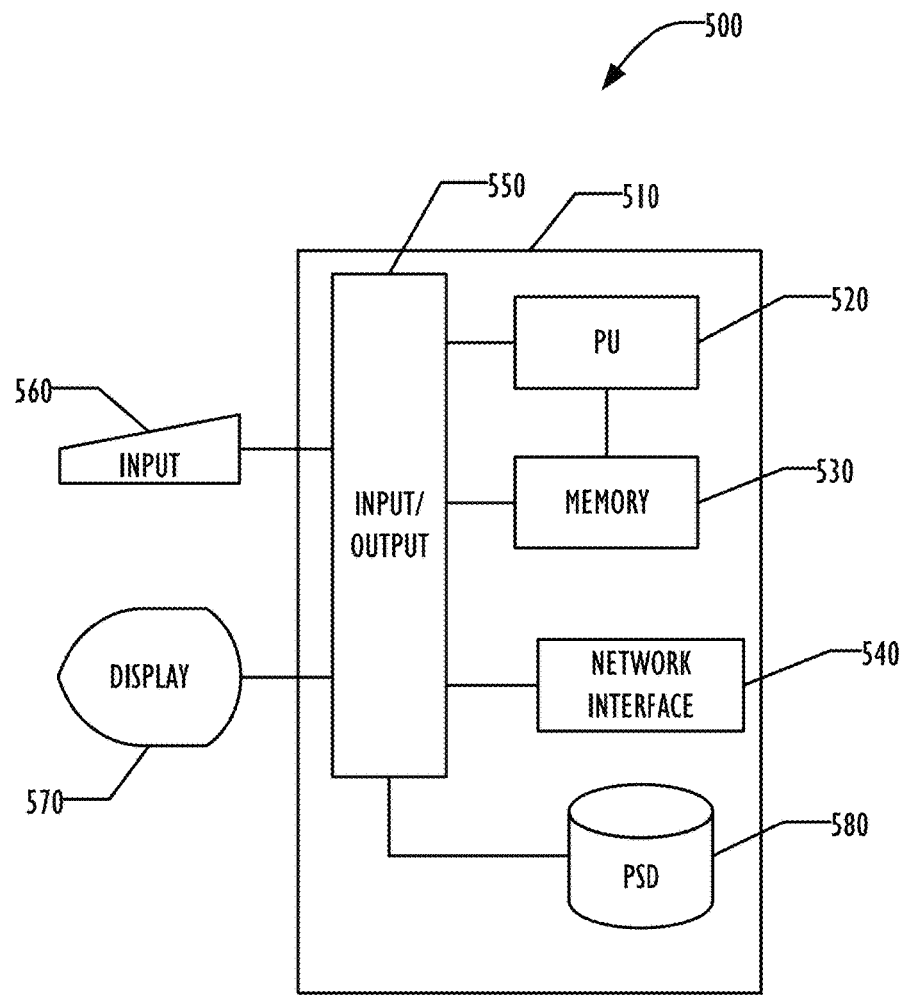
FIG. 5 is a block diagram illustrating a computer system for use in implementing one or more embodiments.

Referring now to FIG. 5, an example computer 500 for use as one of the servers 180-190 is illustrated in block diagram form. Example computer 500 comprises a system unit 510 which may be optionally connected to an input device or system 560 (e.g., keyboard, mouse, touch screen, etc.) and display 570. A program storage device (PSD) 580 (sometimes referred to as a hard disc) is included with the system unit 510. Also included with system unit 510 is a network interface 540 for communication via a network with other computing and corporate infrastructure devices (not shown). Network interface 540 may be included within system unit 510 or be external to system unit 510. In either case, system unit 510 will be communicatively coupled to network interface 540. Program storage device 580 represents any form of non-volatile storage including, but not limited to, all forms of optical and magnetic, including solid-state, storage elements, including removable media, and may be included within system unit 510 or be external to system unit 510. Program storage device 580 may be used for storage of software to control system unit 510, data for use by the computer 500, or both.

System unit 510 may be programmed to perform methods in accordance with this disclosure (an example of which is in FIG. 4). System unit 510 comprises a processor unit (PU) 520, input-output (I/O) interface 550 and memory 530. Processing unit 520 may include any programmable controller device, such as microprocessors available from Intel Corp. and other manufacturers. Memory 530 may include one or more memory modules and comprise random access memory (RAM), read only memory (ROM), programmable read only memory (PROM), programmable read-write memory, and solid-state memory. One of ordinary skill in the art will also recognize that PU 520 may also include some internal memory including, for example, cache memory.

Embodiments of the system 100 provide for better alarm management. Current solutions do not provide the medical context for the alarm with the alarm. They may provide only a text message with the alarm message, for example: SPO2 LOW 76.

Embodiments of an alarm management system described herein can provide a hospital ICU or nursing administrator with one or more of the following tool set: an alarm dashboard which categorizes and graphs alarms for an alarm environment analysis, an alarm criticality discernment rule set and editor, an alarm context messaging system, and an alarm router rule set and editor. Embodiments of these tools can help identify, track, and monitor problem alarms.

For example, hospitals from time to time initiate efforts to improve alarm management, but have lacked the tools to determine whether any improvements are being made. Use of embodiments of the alarm dashboard can allow an administrator to measure the improvement of alarm management initiatives.

Embodiments of the alarm context messaging system can deliver patient status and relevant physiological data with an alarm in the alarm message, providing medical contexts for the alarm. Embodiments can match time-stamped alarms with the corresponding physiological recorded data coming from multiple and discrete physiological data monitors, allowing nursing staff and administrators to understand better the events causing alarms, as well as to evaluate the usefulness of those alarms. The system can produce a picture of the physiological data which was recorded around the time of the alarm and forward this picture, along with the alarm notification, to a care provider through text message or other suitable device. The system can provide vital signs distributions to healthcare providers to allow them to optimize alarm thresholds.

Embodiments can implement smart alarms and other quality improvement applications on the underlying distributed platform for collecting, archiving, and processing arbitrary data in a healthcare setting such as described above.

Embodiments of the alarm criticality discernment tool can implement alarm criticality discernment rules to help prioritize alarms.

Embodiments of the alarm router tool can change how alarms are routed and who should receive the alarms.

Embodiments of the alarm dashboard can display alarm history and trends categorized any way the administrator desires, for example, by type, frequency, criticality, false positive and false negative (as detected), alarm load per shift, alarm load per clinician, alarm load per patient, alarm load per bed and unit, alarm load by disease, or other factors to be determined by the care provider or administrator. The alarm dashboard is primarily an administrative tool, allowing administrators to understand the way in which alarms are occurring and are being addressed.

The alarm criticality discernment (ACD) tool is a set of rules for distinguishing critical from non-critical alarms and an editor to manage the rules. This rule set can include hospital policy for setting or re-setting alarm thresholds or silencing alarms and other alarm related policies. Rules can include computational algorithms. The ACD tool can also accommodate doctor's orders about alarm settings allowing a clinician to determine rules or exceptions for individual patients. The editor is used to view, modify and apply rules.

The ACD tool is dynamic in that the rules may change over time to allow for changes in the maturity of the patient, acuity, and diagnosis. For example, a neonatal patient changes significantly over time, and the rules applicable to that patient are preferably dynamic as well, unlike rules that would apply to industrial processes. The ACD tool is based, in part, on over 40 bed-years of data from hospital sources and analysis of interactions between such physiological processes. The rules can be disease specific, consider the source of the alarms, and the way in which measured data vary, including thresholds and histograms of trends of data.

The rules generated for the ACD tool can be manually adjusted to accommodate patient or doctor specific variances.

The alarm renderer tool is a program that runs on the system 100 for a specific patient that, upon receiving a patient alarm from a monitoring device, renders a set of pictures of the physiological data before the alarm. This picture can be forwarded to a care provider to allow them to determine if the alarm is critical or if it is a false alarm.

Currently a nurse may be asked to describe verbally to a physician what is on a bedside monitor for a specific patient during an alarm event. Such verbal communication raises not only the possibility of miscommunication, but also patient privacy concerns under the Health Insurance Portability and Accountability Act (HIPAA). The alarm renderer tool can provide a context-specific visual picture in conjunction with the alarm which can be forwarded to the physician. The physiological data provided with the alarm can thus provide more than what a nurse viewing a patient monitor could see. The data provided by the alarm renderer tool can be historical data that has been generated, captured and stored by a server over the course of monitoring this patient. The amount of data provided with the alarm may be context specific, patient specific, and physician specific. In one embodiment, as each patient is admitted to the facility, a record is designed specifically for that patient to allow data to be generated, captured and stored as soon as the patient is connected to the patient monitoring sensors.

The alarm router tool is a set of rules and editor for routing and escalating unacknowledged alarms to other care providers and recording these events, as well as generating meta-alarms or policy alarms when, for example, a care provider is dealing with an alarm flood (e.g., greater than 10 alarms in 10 minutes for one operator). The alarm routing tool may direct the right alarms to the right care givers. For example, a ventilator alarm goes to the respiratory therapist while a code alarm goes to the crash team. Escalation rules can also be included. For example, only critical alarms go to the charge nurse as opposed to all alarms. The alarm management system can respond to alarm floods by sending notifications requesting extra support on the floor to deal with the heavy alarm load.

Alarms have different ways of being broadcast. Primary notification systems include visual lights, auditory alarms, and nurse call stations. Secondary notification systems include pagers, alarm phones, etc. These secondary systems tie into 1) bedside devices, 2) middleware vendor systems, 3) end point device systems, 4) call buttons and phones in the rooms. The alarm router tool allows routing of alarms based on the specific problem indicated by the alarm. Although particular alarms are typically used in ICU-type settings, any hospital system that uses patient telemetry units may generate alarms to a central monitoring station and can benefit from the alarm router tool techniques.

The alarm router tool uses a context of the alarm to determine the routing decisions. The alarms are routed through one or more servers that can process and route the alarms. In some embodiments, the system employs multiple servers using load balancing techniques. The data from the monitors is intercepted and recorded in a real-time using a customized computer system. An arbitrary number of programs may be instantiated to do the data processing as desired.

The data can be de-identified to avoid HIPAA concerns and allowing some embodiments to use offsite servers, such as cloud-based servers. The alarm router tool uses the informatics servers 180 of the system 100 to collect all of the medications, lab results, admit transfer/discharge records, and physiological data from networked and non-networked bedside monitor equipment 120, including devices with serial (120B) and analog outputs (120C). The alarm router tool uses rules and editor to route the alarms appropriately based on the context.

The rules and editor are based on expert knowledge of doctors and nurses and alarm filtering. Embodiments may provide multiple sets of alarm profiles for different types of patient conditions. Primary alarms are alarms that must be responded to, while secondary alarms are events or conditions that help a nurse determine why an alarm is going off. Audible alarms sounded by bedside monitors 120 are typically considered primary alarms. Text messages that may be generated to notify a nurse that a bedside alarm is going off are considered secondary alarms. Secondary alarms connect the alarms to additional people as designated in the unit protocol.

Not all alarms are equally critical. While all alarms should be responded to, they can be responded to in different ways. ICUs find that constant alarms not only keep nurses from responding appropriately, because there are too many to handle, but also tend to cause patient distress from the constancy of all the alarms ringing in their area. By allowing primary alarms to be set to critical thresholds as determined by the care provider and by moving alarms to the alarm router, the alarm router tool can become the primary alarm for certain alarms, eliminating staff and patient stress and annoyance.

The alarm router tool can also escalate alarms, so that, for example, alarms that are not answered can be routed to additional designated people, or in another example, alarms that require additional people to respond can be routed to them directly to help manage the situation.

Embodiments of the alarm management system can enable better communications between nurses, doctor, and patients. Alarm routing is implemented by rules that can be edited by an administrator, and may apply arbitrary calculations for recognizing false positives and false negatives. The alarm management system may provide rules for discriminating between critical and non-critical alarms, implemented as rules that can be edited by an administrator.

In addition to intelligent routing of alarms, embodiments can capture relevant physiological data associated with an alarm and can provide that physiological data in a visual display. Alarm thresholds can be set based on institutional and other recommended alarm threshold guidelines based on physiological data streams. Embodiments can automatically detect appropriate thresholds based on analysis of physiological data. The rendered patient physiological data associated with the alarm may be sent through e-mail, text message, or other designated devices to alarm recipients.

Alarms may be routed based on criticality of alarm and some alarms may be filtered to reduce nuisance alarms. Alarms can be segmented based on criticality or other criteria. For example, critical monitor thresholds may be associated with highest priority alarms for broadcast or sent to all responders while less critical monitor thresholds may be associated with lower priority alarms and sent to a reduced set of responders. In one embodiment, the physiological data from the bedside monitors 120 may be processed in real-time for various priorities of alarms, which can be targeted to a designated set of responders. For example, critical high priority alarms can be routed to special response teams.

Embodiments of an alarm management system may provide an alarm dashboard for administering the alarm management system. The alarm dashboard may provide scheduled analysis and report generation of alarm data, as well as user driven analysis. The alarm management system allows ICU administrators to understand and manage their alarm environment better. The alarm dashboard allows ICU administrators to enforce policy or track policy variations by care providers.

Figure 6:
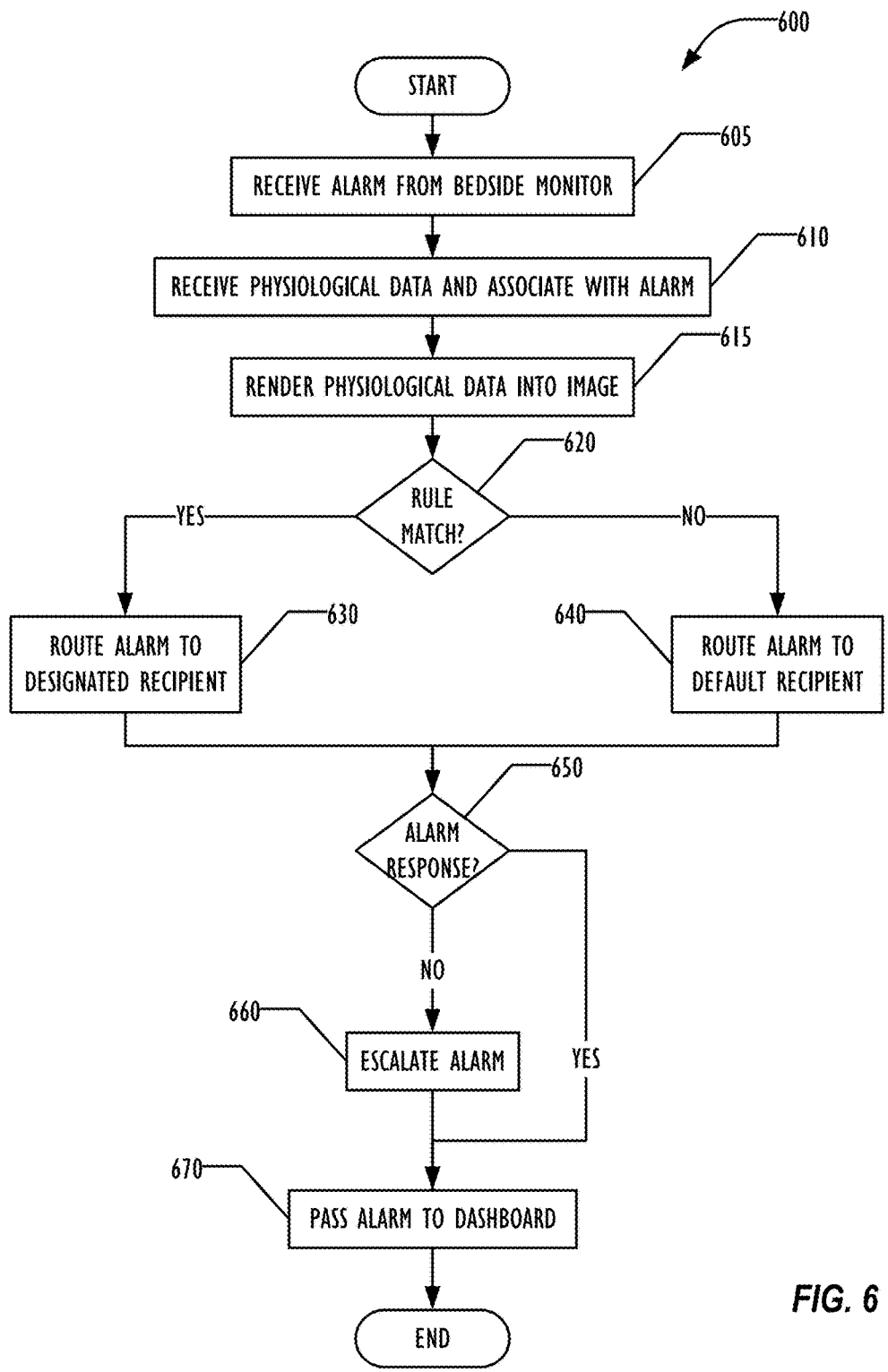
FIG. 6 is a flowchart illustrating a technique for rule-based processing of alarms according to one embodiment.

Turning to FIG. 6, a flowchart illustrates a technique 600 for managing alarms. In block 605, an informatics server 180 receives an alarm from one of the bedside monitors 120. In block 610, physiological data corresponding to that bedside monitor is received and associated with the alarm. In some embodiments, the physiological data may be current physiological data. In other embodiments, the physiological data may be a set of physiological data for an immediate past period of time, such as for the 30 seconds prior to the time of the alarm, which has been previously received and stored by the informatics server 180. In some embodiments, the physiological data is rendered into an image that can be attached to the alarm indication in block 615. A set of alarm rules may then be evaluated. Although a single rule evaluation is illustrated for clarity in FIG. 6, any number of rules may be evaluated as necessary. When a rule matches (620) the conditions of the alarm, including medical context information provided by the physiological data, then in block 630 the alarm and image may be routed using any desired transmittal technique to a recipient or type of recipient specified in the rule. If no rule matches the alarm, then in block 640 the alarm and physiological data may be routed to a default recipient or type of recipient. A rule may specify more than one recipient for the alarm, and may specify the recipient in any convenient way, such as by type or role of recipient.

In block 650, the alarm management system monitors response to the alarm. If the alarm is not answered in a predetermined length of time that may be configured according to unit or facility policy, or as defined by a doctor for the specific patient, the alarm may be escalated in block 660 and routed to an additional person or group of persons. Similarly, although not illustrated in FIG. 6, if multiple alarms are received within a predetermined time period and the number exceeds a predefined threshold (an "alarm flood"), the escalation procedure may route the alarm to additional recipients to obtain additional help in responding to the alarm flood. Finally, in block 670, data about the alarm may be passed to the alarm dashboard tool, for use by administrative staff.

Figure 7:
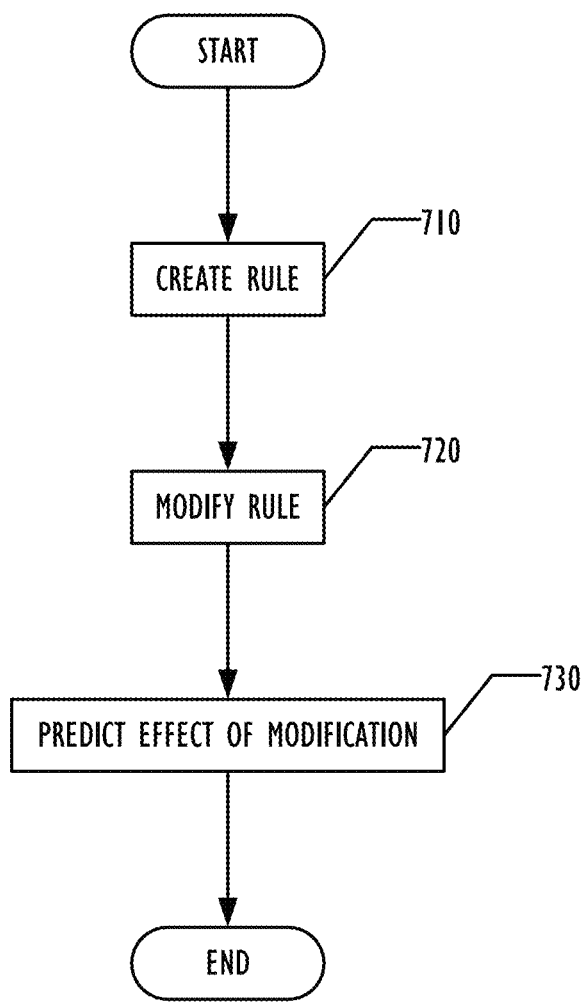
FIG. 7 is a flowchart illustrating a technique for establishing a rule for processing alarms according to one embodiment.

FIG. 7 is a flowchart illustrating a rule creation and editing process according to one embodiment. In block 710 a rule editor may be used to create a rule. In block 720, the rule editor may be invoked to modify the rule. In block 730, the alarm management system may provide an indication predicting the effect of the rule, including showing how the change would have affected previous alarm handling based on historical data.

Figure 8:
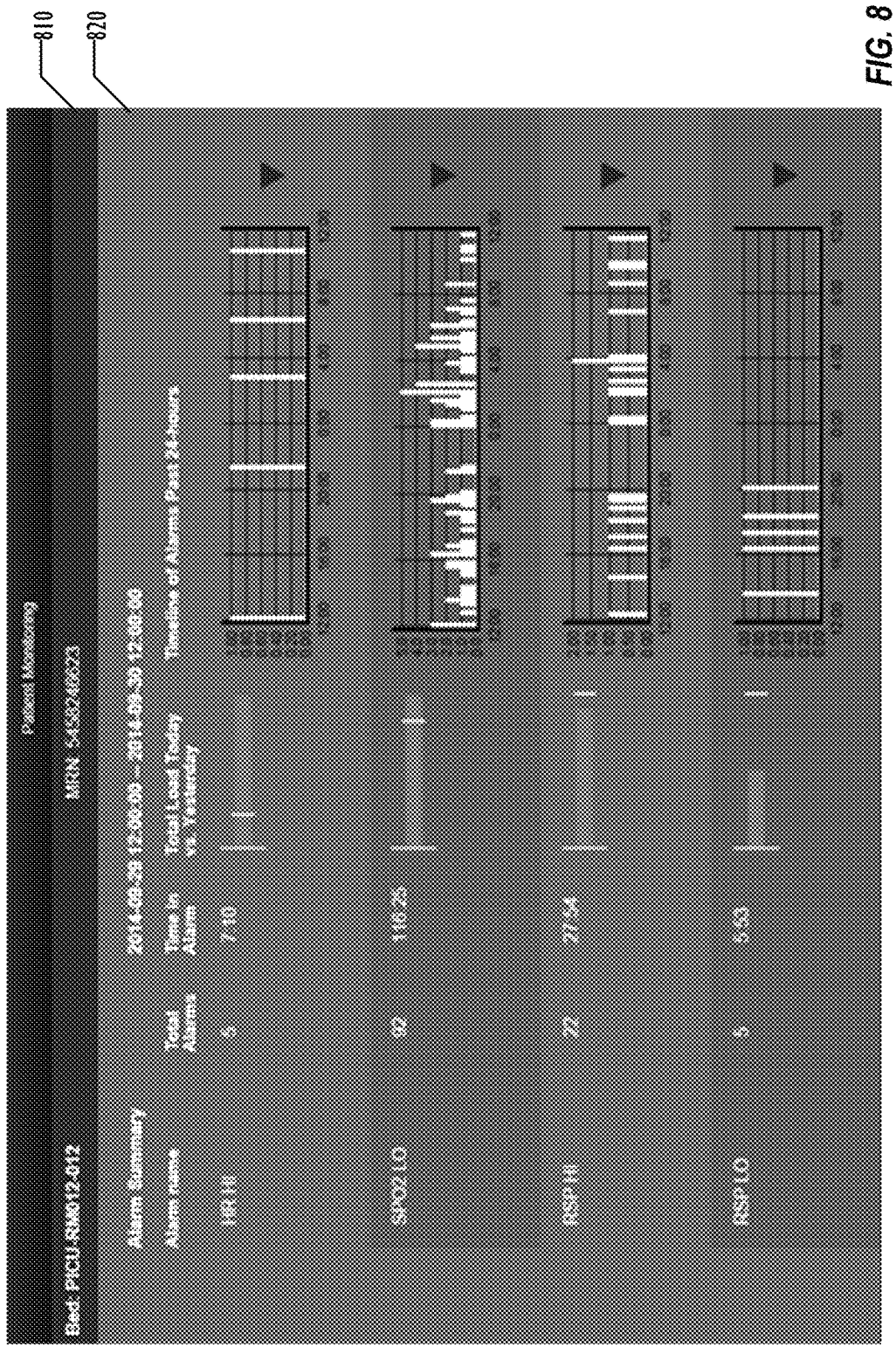
FIGS. 8-14 are screenshots illustrating displays provided by a hospital system according to one embodiment.
Figure 9:
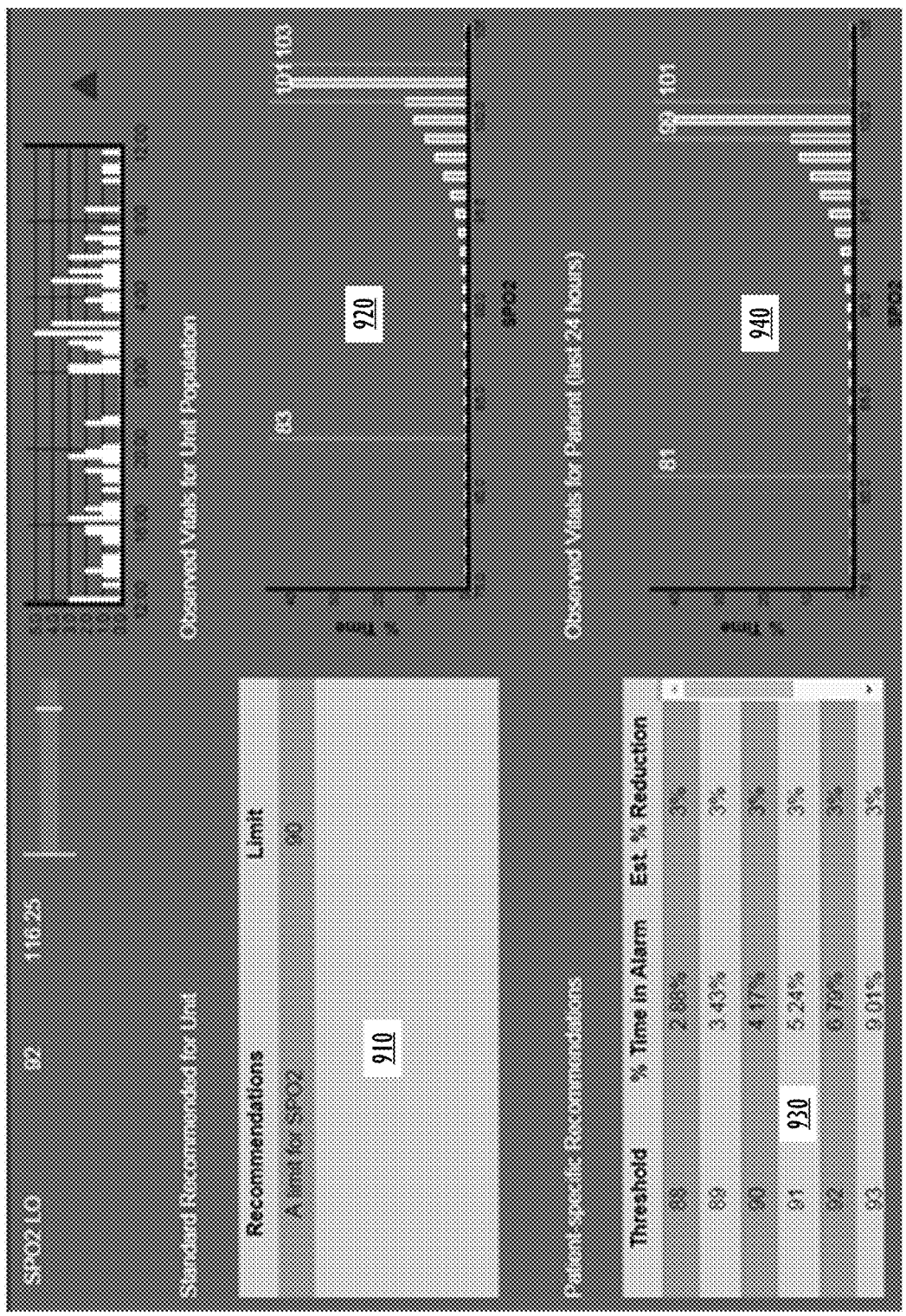

FIGS. 8 and 9 are example screenshots illustrating patient alarm data monitoring in the system 100 according to one embodiment. In this example, a clinician assigns a patient alarm data monitor to the patient. The system 100 then displays a screen as illustrated in FIG. 8.

Line 810 contains patient and bed information such as the patient's name, unit and bed number, patient identification number, and date of birth, in this example "Bed: PICU-RM012-012" and "MRN 5458246623." Area 820 is a patient's alarm summary indicating the period from admission to the present. In the area 820 is a table with a row for each type of alarm the patient has experienced. The first row of area 820 is the column headings (in this example, alarm name, total alarms, time in alarms, total load today vs. yesterday, and timeline of alarms past 24 hours). The clinician can select from the list of alarms.

When the clinician selects an alarm, for example, "SpO2 LOW," the system 100 displays a recommendation screen illustrated in FIG. 9. Area 910 is the Standard Recommended for Unit with the recommended Limit set by Hospital policy for typical patients in that unit.

Area 920 displays "Observed Vitals for Unit Population," which is a histogram of this unit's typical patient alarm values for a sample of the past 25 hours, excluding the last hour. The first percentile value, the 50th percentile value, and the 99th percentile value are marked in the histogram. In this example the typical patient in this unit had an SpO2 Low alarm value at or below 83 in only 1% of the sample, a value of 100 at or below in 50% of the sample (the mean), and a value at or below 103 in 99% of the sample.

Area 930 displays "Patient-specific Recommendations" as a chart displaying a calculated matrix showing: for each threshold value the % of time in alarm (for the most recent 25 hours, excluding the last hour) and an estimated % reductions possible, if the alarm limits are set at that threshold.

In area 940, "Observed Vitals for Patient" are displayed as a histogram of this patient's alarm values for the past 25 hours, excluding the last hour. As in area 920, the first percentile value, the 50th percentile value, and the 99th percentile value are marked. In this example, the patient in this unit had an SpO2 Low alarm value at or below 81 in only 1% of the sample, a value of at or below 98 in 50% of the sample (the mean), and a value at or below 100, in 99% of the sample. Using area 940, a clinician can determine the patient's current baseline. With the patient-specific recommendations in area 930, a Clinician can decide on an alarm threshold that balances prompt notice against unnecessary alarms.

FIGS. 10-14 are screenshots illustrating example alarm dashboard displays provided by an embodiment of the system 100. An alarms analytics dashboard application draws a clear picture of all the Alarms that go off in a clinical units. In one embodiment, it compares the alarms over the last shift (short interval) with the recent past, a long interval of 90 days.

The intended user of the alarm analytics dashboard application is a clinician manager. This person typically has responsibilities that require them to understand the alarm environment of a unit or several units or the entire hospital. The clinician manager can use the information to recommend or implement policy changes in how alarms are handled, changes in staffing loads, or allocations between units, etc.

Figure 10:
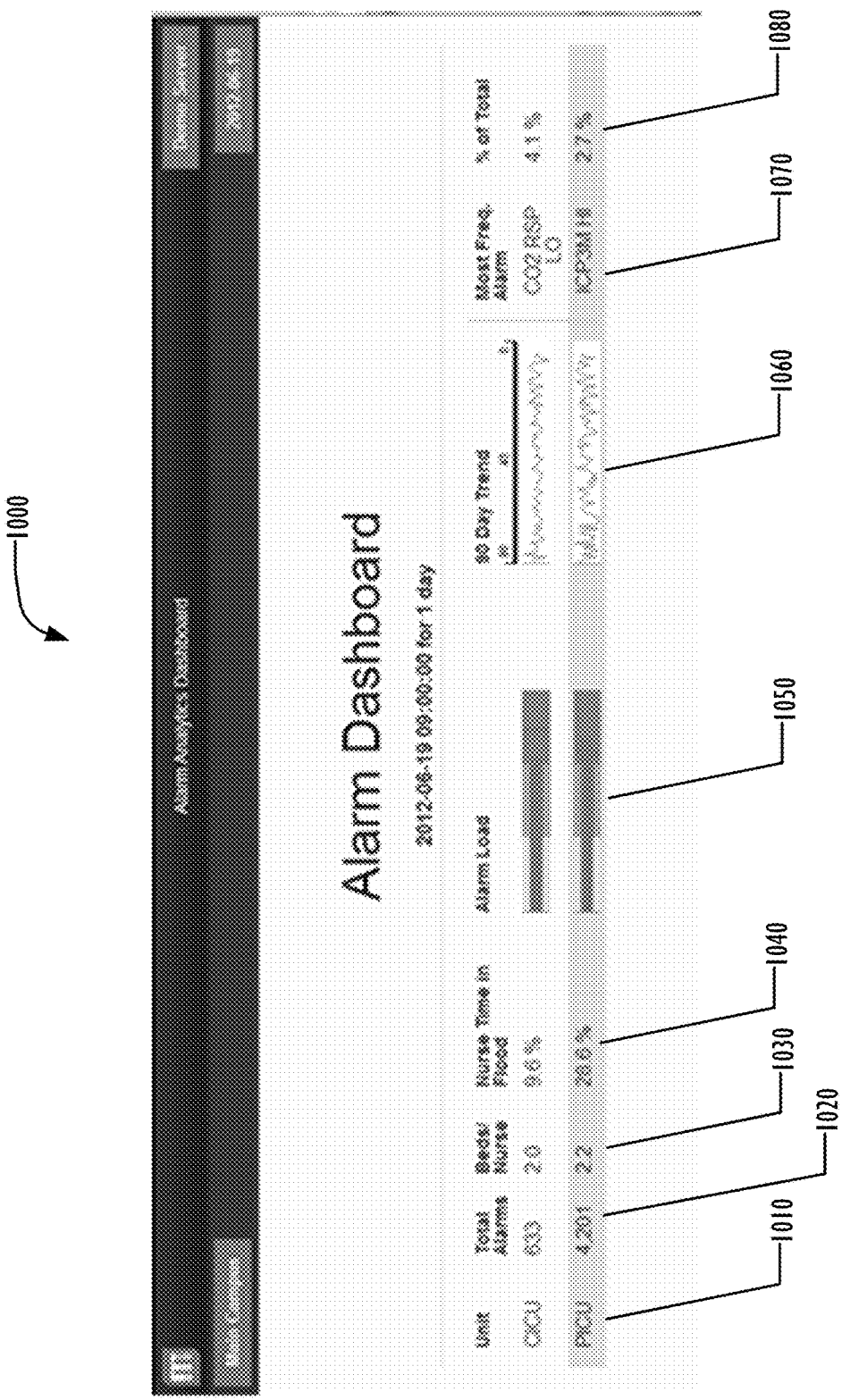

FIG. 10 illustrates a basic alarm dashboard screen 1000 that characterizes the hospital's alarm environment for the last short time interval (e.g., a 24 hour day or perhaps an 8 or 12 hour shift), relative to some long time interval, such as the last 90 days. The length of the short and long time intervals can be configured. Each unit (1010) is displayed in a separate row. The dashboard in this example shows for the last short time interval total alarms in each unit (1020), an average number of beds a nurse in that unit handled (1030), a percentage of time nurses were in an alarm flood state (1040), a most frequent alarm in the unit (1070), and a percentage of all alarms for that most frequent alarm in the unit (1080). In addition, a trend graph 1060 shows a plot line for the number of alarms across the long time interval.

Centered in the dashboard 100 is an alarm load graph 1050 that shows the total number of alarms in the short time interval as a horizontal bar, and on the same scale shows that total relative to the long interval's (90 day) moving average displayed as a vertical bar. There are three distinct areas that indicate whether the alarm load has been manageable (in this embodiment, 0-150 alarms/RN/shift), likely manageable (150-300 alarms/RN/shift), or unmanageable (>300 alarms/RN/shift) during the last short time interval. The displayed values are calculated off of the staffing ratio and observed alarms for that unit during the short and long time intervals.

Figure 11:
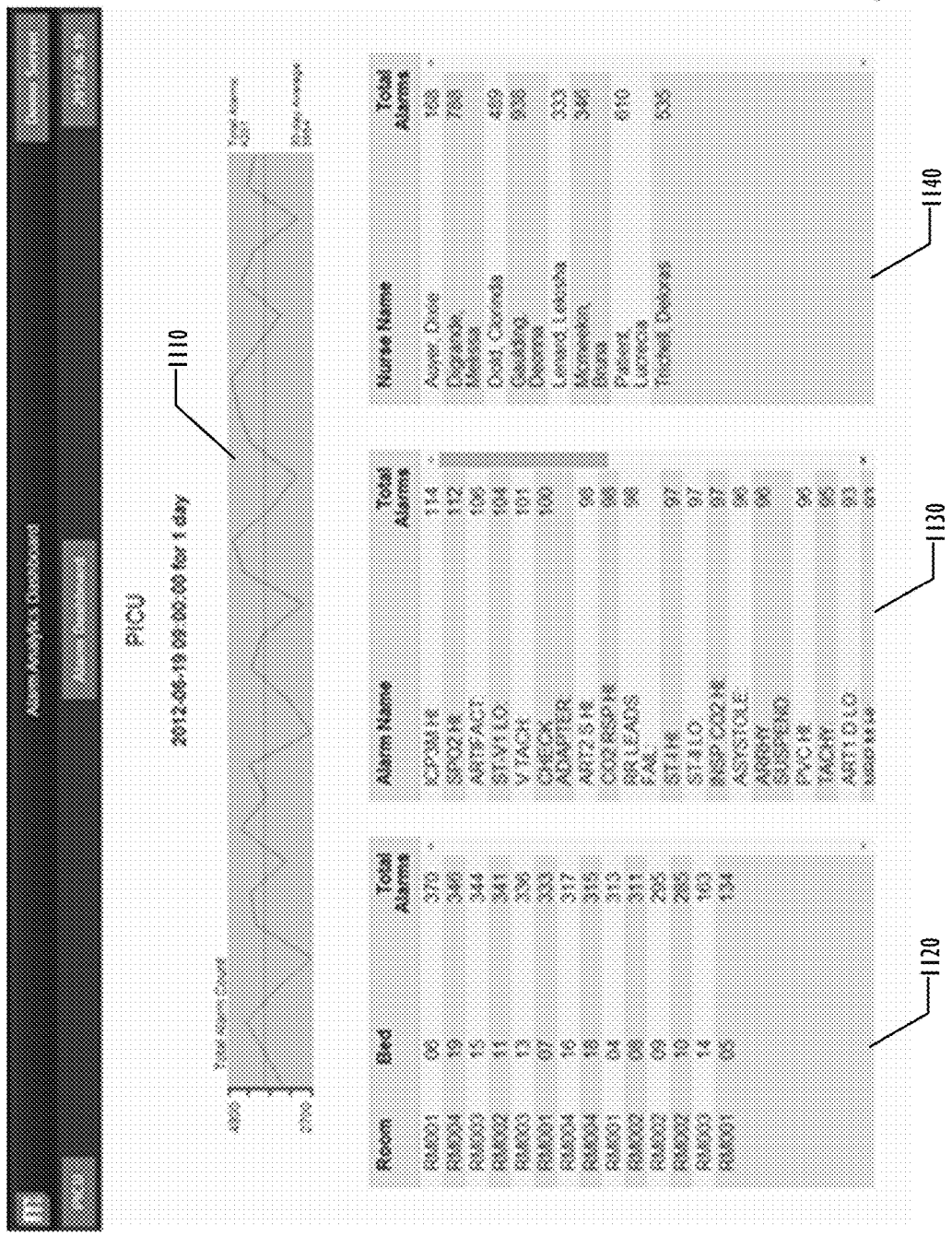

FIG. 11 illustrates a unit analytics screen of the system 100 according to one embodiment that allows a clinician manager to examine alarm data for a particular unit. The screen characterizes the hospital's alarm environment for the last short time interval (e.g., an 8 or 12 hour shift), relative to some long time interval, such as the last 90 days. The length of the short and long time intervals can be configured. The unit analytics screen identifies the unit and the time interval shown.

A total alarm count graph 1110 plots the number of alarms (for each short time interval) over the last long time interval. In one embodiment, the display also includes a count of total alarms and a 30-day average value that displays the floating average over the last long time interval.

Area 1120 displays the number of alarms in the last short time interval for each bed in the unit. In one embodiment, the clinician manager can drill down by selecting a bed, allowing the clinician manager to open a display (FIG. 12) of all alarms from that bed. Area 1130 displays a table of alarm types and alarm counts for the last short time interval. A clinician manager can similarly drill down on this display, producing a display (FIG. 13) of all beds and clinic staff that had that alarm type. Area 1140 displays a table of nursing staff and alarm counts in the last short time interval. The clinician manager can drill down to open a display (FIG. 14) of all beds and alarm types for that clinic staff member during the last short time interval.

Figure 12:
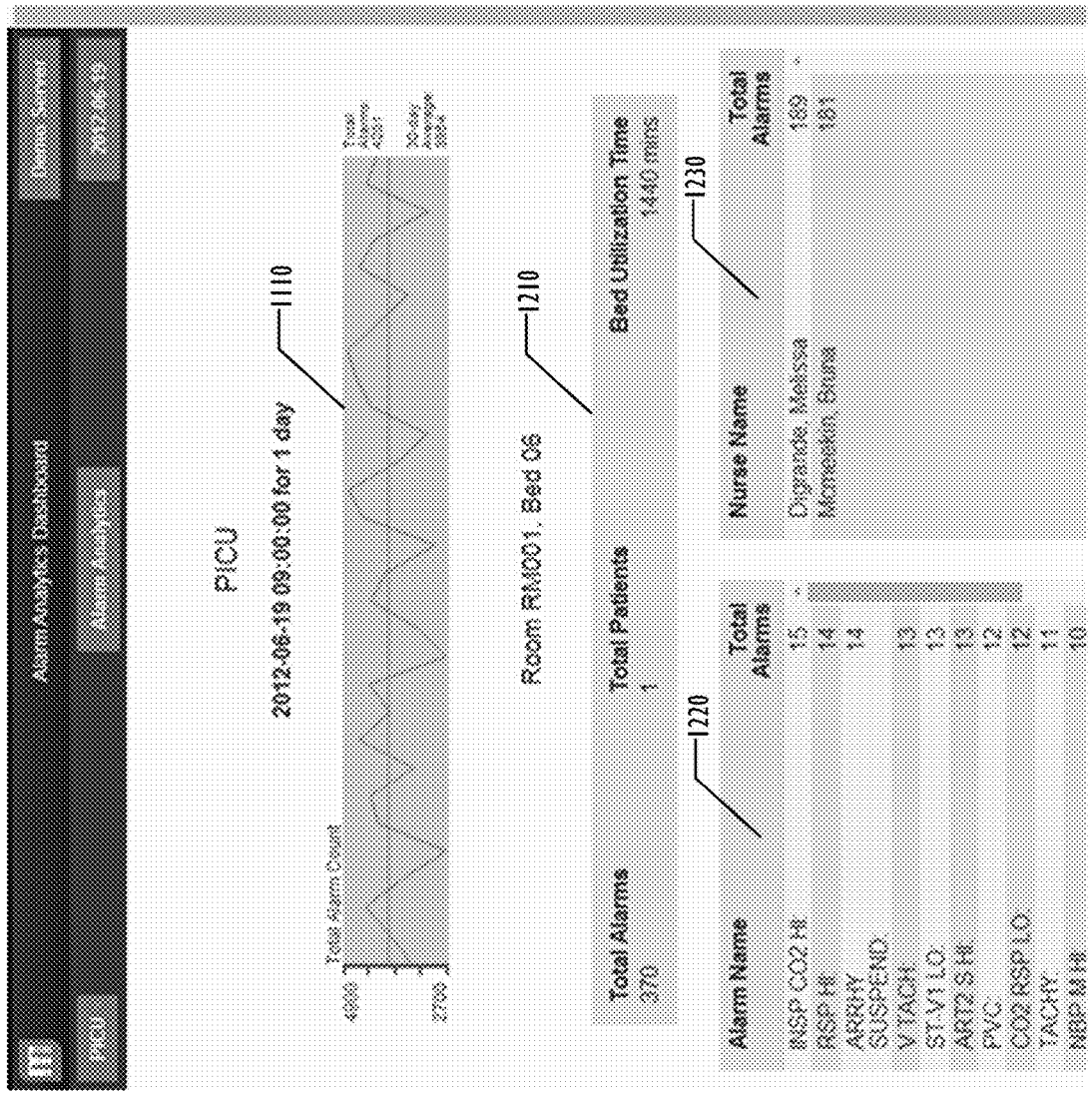

FIG. 12 is an example screenshot illustrating an alarms by bed display by the system 100 according to one embodiment. In this example, the total alarm count timeline 1110 of FIG. 11 is repeated on the alarms by bed display. But the breakdowns below the timeline 1120 are now limited to the specific bed, in this example "Room RM001, Bed 06." A summary area 1210 indicates the total number of alarms that occurred during the short time interval, the total number of unique patients to use the bed during the last short time interval, and the total time during the short interval that a patient was admitted to the bed.

Table 1220 displays alarm types for that bed during the last short time interval. Table 1230 displays the clinical staff assigned to that bed during the last short time interval and their alarm counts.

Figure 13:
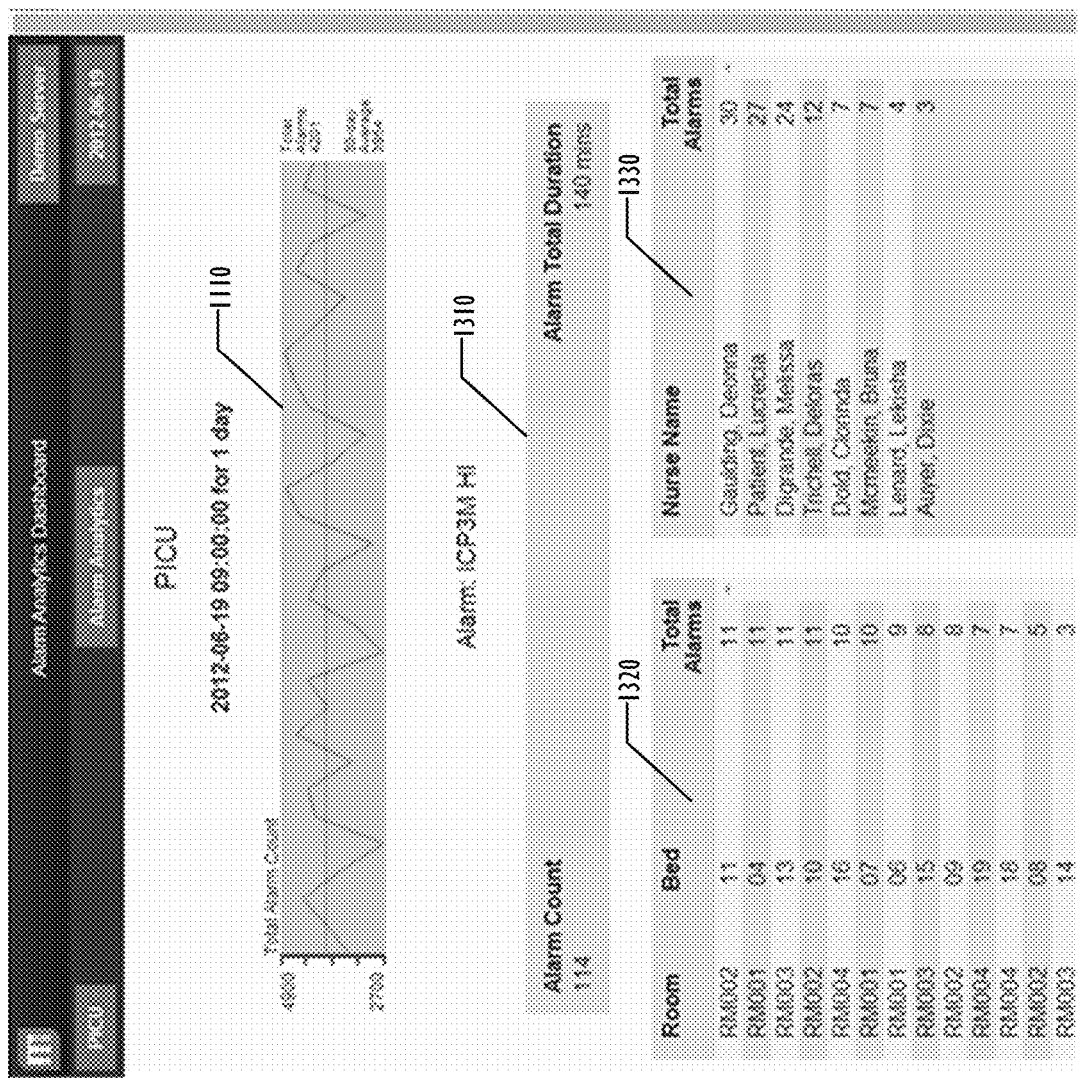

From here, the clinician manager can select an alarm type or a clinic staff name and the system 100 will display that page of the dashboard. FIG. 13 is an example screenshot illustrating a dashboard display of the system 100 according to one embodiment that displays alarms for a specific alarm type, in this example "ICP3M HI." As with FIGS. 11-12, the total alarms for the unit are displayed in timeline 1110. In addition, area 1310 display a count of the selected alarm type that occurred during the last short time interval and a total time that particular alarm was active during the short time interval.

Table 1320 displays the number of alarms of that type by bed during the last short time interval. Table 1330 displays for each clinical staffer the number of alarms of that type received during the last short time interval. By selecting a bed or a clinical staff person, the clinician manager can drill down to the appropriate display.

Figure 14:
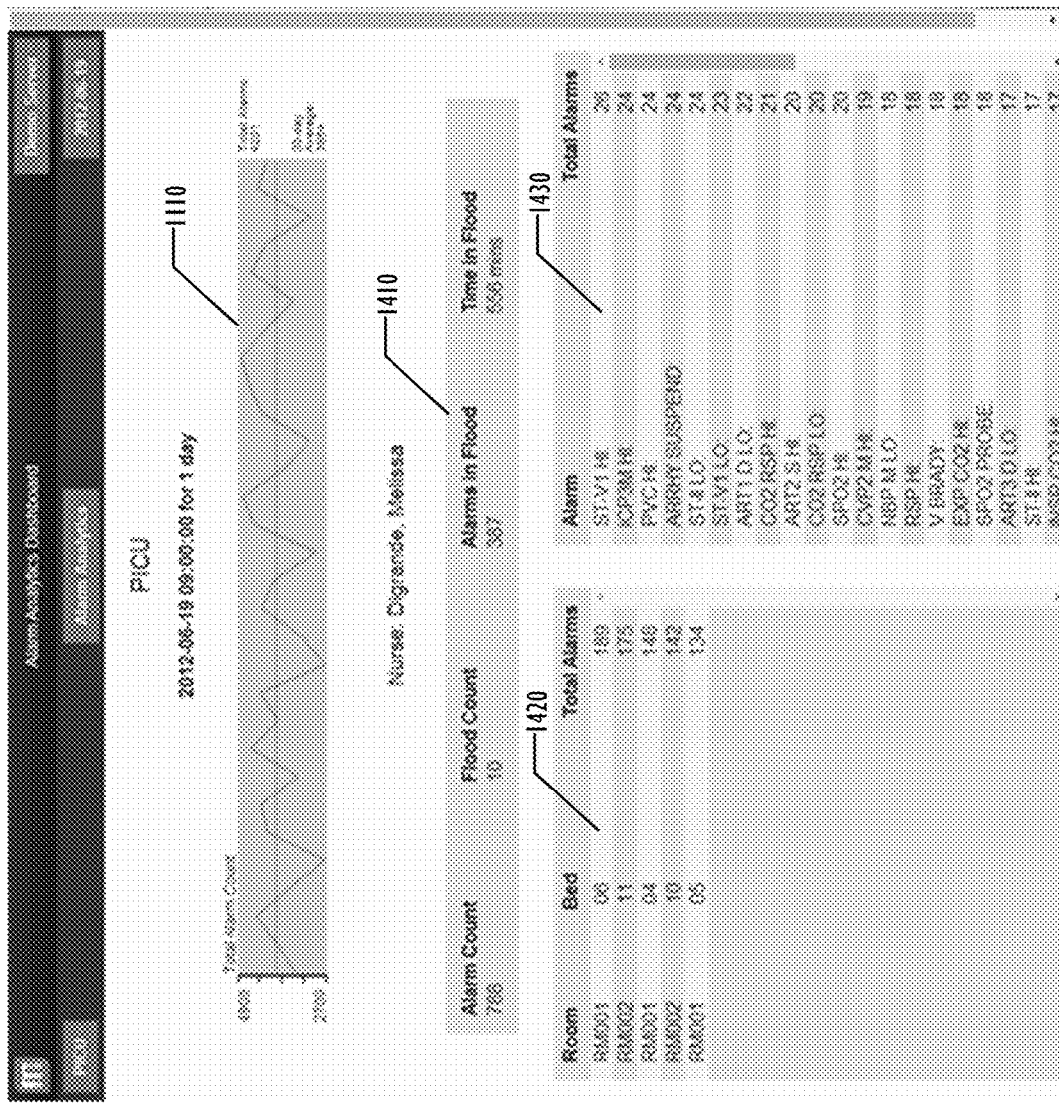

FIG. 14 is an example screenshot illustrating a dashboard display of the system 100 according to one embodiment that displays alarms for a selected clinical staff person. As with FIGS. 11-13, the total alarms for the unit are displayed in timeline 1110.

Summary area 1410 displays information associated with the indicated clinical staff person during the last short time interval, in this example a total count of alarms, a flood count, the total alarms that were included in all the floods, and the total time this particular clinical staff person experienced an alarm flood condition.

Table 1420 displays alarms by bed for all beds assigned to the selected clinic staff member during the last short interval. Table 1430 displays alarms by type received by the selected clinic staff person during the last short time interval. From here the clinician manager can select the bed or alarm type to view the displays of FIG. 12 or 13, or return to the display of FIG. 11 to display information for the unit.

The screenshots of FIGS. 10-14 are illustrative and by way of example only, and other screens, screen layouts, and content may be displayable in an alarm dashboard as desired. In some embodiments, the dashboard is configurable by the clinician manager or other staff to customize the information displayed.

While certain exemplary embodiments have been described in details and shown in the accompanying drawings, it is to be understood that such embodiments are merely illustrative of and not devised without departing from the basic scope thereof, which is determined by the claims that follow.

We claim:

1. An alarm management system, comprising:
an informatics server, comprising:
one or more processors;
a memory, coupled to the one or more processors, on which instructions are stored, comprising instructions that when executed cause one or more processors to:
receive an alarm from a bedside physiological monitoring device;
evaluate an alarm routing rule corresponding to the alarm, the rule associated with an alarm context, comprising patient status and physiological data associated with the alarm, wherein the physiological data associated with the alarm comprises historical data generated over a course of patient monitoring;
route the alarm to a recipient designated by the alarm routing rule;
establish an alarm threshold for the alarm; and
predict effects of modifying the alarm threshold, responsive to historical physiological data; and
a substation, coupled between the bedside physiological monitoring device and the informatics server, programmed to:
insert a timestamp into non-timestamped data received from the bedside physiological monitoring device; and
eliminating clock drift by synchronizing a clock of the substation with a clock of the informatics server.

2. The alarm management system of claim 1, wherein the instructions further comprise instructions that when executed cause one or more processors to:
receive physiological data from the bedside physiological monitoring device;
associate the physiological data with the alarm; and
route the physiological data to the recipient with the alarm.

3. The alarm management system of claim 2, wherein the instructions that when executed cause one or more processors to associate the physiological data with the alarm comprise instructions that when executed cause one or more processors to:
render an image of the physiological data.

4. The alarm management system of claim 1, wherein the instructions further comprise instructions that when executed cause one or more processors to:
aggregate alarm information from multiple patients for display as aggregate values in an alarm dashboard.

5. The alarm management system of claim 1, wherein the instructions that when executed cause one or more processors to route the alarm comprise instructions that when executed cause one or more processors to:
escalate an unanswered alarm to another recipient who can respond to the unanswered alarm.

6. The alarm management system of claim 1, wherein the instructions that when executed cause one or more processors to evaluate an alarm routing rule comprise instructions that when executed cause one or more processors to perform a computation as part of the evaluation of the rule.

7. A non-transitory machine readable medium on which are stored instructions, comprising instructions that when executed cause one or more programmable devices to:
receive an alarm from a bedside physiological monitoring device;
evaluate an alarm routing rule corresponding to the alarm, the rule associated with an alarm context, comprising patient status and physiological data associated with the alarm, wherein the physiological data associated with the alarm comprises historical data generated over a course of patient monitoring;
establish an alarm threshold for the alarm;
predict effects of modifying the alarm threshold, responsive to historical physiological data;
route the alarm to a recipient designated by the alarm routing rule; and
synchronize a first clock with a second clock associated with a substation that injects a timestamp into non-timestamped data received from the bedside physiological monitoring device.

8. The machine readable medium of claim 7, wherein the instructions further comprise instructions that when executed cause one or more programmable devices to:
receive physiological data from the bedside physiological monitoring device;
associate the physiological data with the alarm; and
route the physiological data to the recipient with the alarm.

9. The machine readable medium of claim 8, wherein the instructions that when executed cause one or more programmable devices to associate the physiological data with the alarm comprise instructions that when executed cause one or more programmable devices to:
render an image of the physiological data.

10. The machine readable medium of claim 7, wherein the instructions further comprise instructions that when executed cause one or more programmable devices to:
aggregate alarm information from multiple patients for display as aggregate values in an alarm dashboard.

11. The machine readable medium of claim 7, wherein the instructions that when executed cause one or more programmable devices to route the alarm comprise instructions that when executed cause one or more programmable devices to:
escalate an unanswered alarm to another recipient who can respond to the unanswered alarm.

12. The machine readable medium of claim 7, wherein the instructions that when executed cause one or more programmable devices to evaluate an alarm routing rule comprise instructions that when executed cause one or more programmable devices to perform a computation as part of the evaluation of the rule.

13. A method of managing physiological alarms, comprising:
receiving an alarm from a bedside physiological monitoring device;
injecting a timestamp into non-timestamped data received from the bedside physiological monitoring device;
synchronizing clocks to eliminate clock drift;
evaluating an alarm routing rule corresponding to the alarm, the rule associated with an alarm context comprising patient status and physiological data associated with the alarm, wherein the physiological data associated with the alarm comprises historical data generated over a course of patient monitoring;
establishing an alarm threshold for the alarm;
predicting effects of modifying the alarm threshold, responsive to historical physiological data; and
routing the alarm to a recipient designated by the alarm routing rule,
wherein the alarm routing rule comprises a computational algorithm for distinguishing critical from non-critical alarms.

14. The method of claim 13, further comprising:
   receiving physiological data from the bedside physiological monitoring device;
   associating the physiological data with the alarm; and
   routing the physiological data to the recipient with the alarm.

15. The method of claim 14, wherein associating the physiological data with the alarm comprises:
   rendering an image of the physiological data.

16. The method of claim 13, further comprising:
   aggregating alarm information from multiple patients for display as aggregate values in an alarm dashboard.

17. The method of claim 13, wherein routing the alarm comprises:
   escalating an unanswered alarm to another recipient who can respond to the unanswered alarm.

* * * * *